US010525051B2

(12) United States Patent
Eldon et al.

(10) Patent No.: US 10,525,051 B2
(45) Date of Patent: *Jan. 7, 2020

(54) COMPOSITIONS AND METHODS FOR ACHIEVING SUSTAINED THERAPEUTIC DRUG CONCENTRATIONS IN A SUBJECT

(71) Applicant: Nektar Therapeutics, San Francisco, CA (US)

(72) Inventors: Michael A. Eldon, Redwood City, CA (US); Shibani S. Harite, Fremont, CA (US); Tamra L. Barker, Davis, CA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/723,981

(22) Filed: Oct. 3, 2017

(65) Prior Publication Data

US 2018/0028525 A1    Feb. 1, 2018

Related U.S. Application Data

(63) Continuation of application No. 14/555,440, filed on Nov. 26, 2014, now Pat. No. 9,801,873, which is a continuation of application No. 13/120,551, filed as application No. PCT/US2009/005284 on Sep. 23, 2009, now Pat. No. 8,906,353.

(60) Provisional application No. 61/173,433, filed on Apr. 28, 2009, provisional application No. 61/106,931, filed on Oct. 20, 2008, provisional application No. 61/099,516, filed on Sep. 23, 2008.

(51) Int. Cl.
*A61K 31/4745* (2006.01)
*A61K 47/60* (2017.01)

(52) U.S. Cl.
CPC .......... *A61K 31/4745* (2013.01); *A61K 47/60* (2017.08)

(58) Field of Classification Search
None
See application file for complete search history.

(56) References Cited

U.S. PATENT DOCUMENTS

| | | |
|---|---|---|
| 5,614,549 A | 3/1997 | Greenwald et al. |
| 5,648,506 A | 7/1997 | Desai et al. |
| 5,681,567 A | 10/1997 | Martinez et al. |
| 5,840,900 A | 11/1998 | Greenwald et al. |
| 5,859,022 A | 1/1999 | Hausheer et al. |
| 5,880,131 A | 3/1999 | Greenwald et al. |
| 5,965,566 A | 10/1999 | Greenwald et al. |
| 6,011,042 A | 1/2000 | Greenwald et al. |
| 6,121,451 A | 9/2000 | Henegar et al. |
| 6,127,355 A | 10/2000 | Greenwald et al. |
| 6,153,655 A | 11/2000 | Martinez et al. |
| 6,194,580 B1 | 2/2001 | Greenwald et al. |
| 6,395,266 B1 | 5/2002 | Martinez et al. |
| 6,403,569 B1 | 6/2002 | Achterrath |
| 6,461,603 B2 | 10/2002 | Bentley et al. |
| 6,608,076 B1 | 8/2003 | Greenwald et al. |
| 6,730,334 B2 | 5/2004 | Zhao |
| 7,744,861 B2 | 6/2010 | Zhao et al. |
| 8,906,353 B2 | 12/2014 | Eldon et al. |
| 2001/0041172 A1 | 11/2001 | Bentley et al. |
| 2002/0182172 A1 | 12/2002 | Bentley et al. |
| 2003/0105275 A1 | 6/2003 | Bentley et al. |
| 2004/0037802 A1 | 2/2004 | Zhao et al. |
| 2004/0058981 A1 | 3/2004 | Lai et al. |
| 2004/0077595 A1 | 4/2004 | Cheng et al. |
| 2005/0112088 A1* | 5/2005 | Zhao ....................... C08L 71/02 424/78.27 |
| 2007/0197575 A1 | 8/2007 | Zhao et al. |
| 2009/0074704 A1* | 3/2009 | Zhao ................ A61K 47/48192 424/78.3 |
| 2015/0087668 A1 | 3/2015 | Eldon et al. |

FOREIGN PATENT DOCUMENTS

| | | |
|---|---|---|
| CN | 101199857 | 6/2008 |
| EP | 0 757 049 | 3/1999 |
| EP | 0 923 566 | 10/2003 |
| WO | WO 97/33552 | 9/1997 |
| WO | WO 98/41562 | 9/1998 |
| WO | WO 99/53951 | 10/1999 |
| WO | WO 00/64486 | 11/2000 |
| WO | WO 01/62299 | 8/2001 |
| WO | WO 01/74402 | 10/2001 |
| WO | WO 02/08789 | 1/2002 |
| WO | WO 03/034167 | 4/2003 |
| WO | WO 03/037384 | 5/2003 |
| WO | WO 03/037385 | 5/2003 |
| WO | WO 2005/028539 | 3/2005 |
| WO | WO 2007/098091 | 8/2007 |
| WO | WO 2008/098178 | 8/2008 |

OTHER PUBLICATIONS

Herben et al. ("Herben") Journal of Clinical Oncology 1999 (17) 1897-1905 (Year: 1999).*
Allegrini, et al., "A pharmacokinetic and pharmacodynamic study on metronomic irinotecan in metastatic colorectal cancer patients," British J. of Cancer, vol. 98, pp. 1312-1319, (2008).
Astruc, et al., "Dendritic Catalysts and Dendrimers in Catalysis," Chem. Rev., vol. 101, pp. 2991-3023, (2001).
Conover, et al., "Camptothecin delivery systems: enhanced efficacy and tumor accumulation of camptothecin following its conjugation to polyethylene glycol via a glycine linker," Cancer Chemother. Pharmacol., vol. 42, pp. 407-414, (1998).
Conover, et al., "Camptothecin delivery systems: the utility of amino acid spacers for the conjugation of camptothecin with polyethylene glycol to create prodrugs," Anti-Cancer Drug Des., vol. 14, pp. 499-506, (1999).

(Continued)

*Primary Examiner* — Jeffrey S Lundgren
*Assistant Examiner* — Michael J Schmitt
(74) *Attorney, Agent, or Firm* — Susan T. Evans (57) ABSTRACT

Provided herein are compounds and methods for achieving a sustained therapeutic effect of small molecule anti-cancer agents when administered in vivo.
Sustained Exposure to Active Metabolite with PEG-Irinotecan

13 Claims, 3 Drawing Sheets

(56) References Cited

OTHER PUBLICATIONS

De Jesus, et al., "Polyester Dendritic Systems for Drug Delivery Applications: In Vitro and In Vivo Evaluation," Bioconj. Chem., vol. 13, pp. 453-461, (2002).
De Vos, et al., "Endothelial cell effects of cytotoxics: balance between desired and unwanted effects," Cancer Treatment Rev., vol. 30, pp. 495-513, (2004).
Greenwald, et al., "Poly(ethylene glycol) Conjugated Drugs and Prodrugs: A Comprehensive Review," Crit. Rev. in Therp. Drug Carr. Sys., vol. 17, No. 2, pp. 101-161, (2000).
Herben, et al., "Phase I and Pharmacokinetic Study of Irinotecan Administered as a Low-Dose, Continuous Intravenous Infusion Over 14 Days in Patients With Malignant Solid Tumors," Journal of Clinical Oncology, vol. 17, No. 6, pp. 1897-1905, (1999).
Houghton, et al., "Efficacy of topoisomerase I inhibitors, topotecan and irinotecan, administered at low dose levels in protracted schedules to mice bearing xenografts of human tumors", Cancer Chemotherapy, vol. 36, pp. 393-403, (1995).
Lalloo, et al., "Pharmacokinetic and pharmacodynamic evaluation of a novel in situ forming poly (ethylene glycol)-based hydrogel for the controlled delivery of the camptothecins," J. of Cont. Rel., vol. 112, pp. 333-342, (2006).
Masuda, et al., "Irinotecan (CPT-11): pharmacology and clinical applications", Critical Reviews in Oncology/Hematology, vol. 24, pp. 3-26, (1996).
Merrouche, et al., "High dose-intensity of irinotecan administered every 3 weeks in advanced cancer patients: a feasibility study", Journal of Clinical Oncology, vol. 15, No. 3, pp. 1080-1086, (Mar. 1997).
O'Reilly, et al., "The clinical status of irinotecan (CPT-11), a novel water soluble camptothecin analogue: 1996", Critical Reviews in Oncology/Hematology, vol. 24, pp. 47-70, (1996).
Qiu, et al., "A hydrogel prepared by in situ cross-linking of a thiol-containing poly(ethylene glycol)-based copolymer: a new biomaterial for protein drug delivery," Biomaterials, vol. 24, pp. 11-18, (2003).
Rowinsky, et al., "A Phase I and Pharmacokinetic Study of Pegylated Camptothecin as a 1-Hour Infusion Every 3 Weeks in Patients With Advanced Solid Malignancies," Journal of Clinical Oncology, vol. 21, No. 1, pp. 148-157, (2003).
Singer, et al., "Conjugation of Camptothecin to Poly-(L-Glutamic Acid)," Ann. N.Y. Acad. Sci., pp. 136-150, (2000).
Warnecke, et al., "Maleimide-oligo(ethylene glycol) Derivatives of Camptothecin as Albumin-Binding Prodrugs: Synthesis and Antitumor Efficacy," Bioconj. Chem., vol. 14, pp. 377-387, (2003).
Xie, et al., "Clinical Pharmacokinetics of Irinotecan and Its Metabolites: A Population Analysis," J. of Clin. Oncology, vol. 20, No. 15, pp. 3293-3301, (Aug. 1, 2002).
Zalipsky, et al., "Attachment of Drugs to Polyethylene Glycols," Eur. Polym J., vol. 19, No. 12, pp. 1177-1183, (1983).
PCT International Search Report corresponding to PCT Application No. PCT/US2009/005284 dated Dec. 23, 2009.
PCT International Preliminary Report on Patentability corresponding to PCT/US2009/005284 dated Apr. 7, 2011.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, pp. 1-46, Catalogue 2003—1st, (Jan. 2003).
NOF Corporation, PEG Derivatives, Phospholipid and Drug Delivery Materials for Pharmaceuticals, pp. 1-50, Catalogue 2003—2nd, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; BIOTINS, 5 pages, (Apr. 2004).
Polypure Products, PEG amines; PEG acids and amino acids; PEG thiols and disulfides; BIOTINS, 5 pages, (Apr. 2005).
Quanta Biodesign, Labeling, Derivatization and Crosslinking Reagents for Biological and Related Materials with dPEG™, pp. 1-38, (Mar. 12, 2004).
Quanta Biodesign, Labeling, Modification and Crosslinking Reagents incorporating our unique monodispersed dPEG™ Technology, pp. 1-31, (Nov. 5, 2004).
Quanta Biodesign, Ltd., Leading innovator, producer and provider of monodisperse discrete PEG™ (dPEG™) derivatives, (Product Catalog), pp. 1-51, (Updated: Jul. 18, 2005).
Quanta Biodesign, Ltd., Leading innovator, producer and provider of monodisperse discrete PEG™ (dPEG™) derivatives, (Product Catalog), pp. 1-51, (Updated: Nov. 17, 2005).
Shearwater Polymers, Inc., Polyethylene Glycol and Derivatives, 50 pages, (Catalog—Mar. 1995).
Shearwater Polymers, Inc., Polyethylene Glycol and Derivatives, 55 pages, (Catalog—Jul. 1997).
Shearwater Polymers, Inc., Polyethylene Glycol and Derivatives: Functionalized Biocompatible Polymers for Research and Pharmaceuticals, pp. 1-50, (Catalog—Jan. 2000).
Shearwater Corporation, Polyethylene Glycol and Derivatives for Biomedical Applications, 20 pages, (Catalog—Jul. 2001).
Nektar Therapeutics Press Release, "New Positive Data Announced for NKTR-102 (PEG-irinotecan), Highlights Promise of Nektar's Innovative Small Molecule PEG-Oncolytics", 3 pages, Jun. 2, 2008.
Australian Patent Examination Report No. 1 corresponding to Australian Patent Application No. 2009297091 dated Aug. 20, 2013.
Canadian Communication corresponding to Canadian Patent Application No. 2,736,939 dated May 21, 2015.
Canadian Communication corresponding to Canadian Patent Application No. 2,736,939 dated Jan. 18, 2016.
Chinese Notification of the First Office Action corresponding to Chinese Patent Application No. 200980137132.6 dated May 11, 2012.
Chinese Notification of the Second Office Action corresponding to Chinese Patent Application No. 200980137132.6 dated Nov. 21, 2012.
Chinese Rejection Decision corresponding to Chinese Patent Application No. 200980137132.6 dated Jun. 6, 2013.
Chinese Reexamination Decision corresponding to Chinese Patent Application No. 200980137132.6 dated Oct. 29, 2013.
Chinese Notification of the Third Office Action corresponding to Chinese Patent Application No. 200980137132.6 dated Nov. 15, 2013.
Chinese Rejection Decision corresponding to Chinese Patent Application No. 200980137132.6 dated Apr. 3, 2014.
Chinese Notification of Reexamination corresponding to Chinese Patent Application No. 200980137132.6 dated Jul. 17, 2015.
European Examination Report corresponding to European Patent Application No. 09 789 364.8-1464 dated Sep. 30, 2013.
European Communication corresponding to European Patent Application No. 09 789 364.8-1466 dated Nov. 28, 2016.
Israeli First Substantive Examination Report corresponding to Israeli Patent Application No. 211888 dated Dec. 26, 2013.
Japanese Notice of Reasons for Rejection corresponding to Japanese Patent Application No. 2011-527834 dated Oct. 31, 2013.
Japanese Notice of Final Rejection corresponding to Japanese Patent Application No. 2011-527834 dated Jul. 15, 2014.
Japanese Notice of Reasons for Rejection corresponding to Japanese Patent Application No. 2014-232556 dated Dec. 1, 2015.
English Translation of Japanese Notice of Final Rejection corresponding to Japanese Patent Application No. 2014-232556 dated May 24, 2016.
Korean Notice of Grounds for Rejection corresponding to Korean Patent Application No. 2011-7005982 dated Jan. 12, 2016.

(56) References Cited

OTHER PUBLICATIONS

English Translation of Korean Notice of Final Rejection corresponding to Korean Patent Application No. 10-2011-7005982 dated Jan. 2, 2017.
Mexican Official Letter corresponding to Mexican Patent Application No. MX/a/2011/003063 dated Jun. 14, 2013.
Canadian Communication corresponding to Canadian Patent Application No. 2,736,939 dated Oct. 14, 2016.
Indian Examination Report corresponding to Indian Patent Application No. 1968/CHENP/2011 dated Jun. 27, 2017.
Korean Notice of Final Rejection corresponding to Korean Patent Application No. 2011-7005982 dated Nov. 24, 2016.
Korean Notice of Final Rejection corresponding to Korean Patent Application No. 2011-7005982 dated Jan. 2, 2017.
Canadian Office Communication corresponding to Canadian Patent Application No. 2,736,939 dated Apr. 4, 2018.

* cited by examiner

| Grp | Treatment Regimen | | | | Median TTE | T-C | TGD (%) | Regressions | | | Statistical Significance | | | |
|---|---|---|---|---|---|---|---|---|---|---|---|---|---|---|
| | Agent | mg/kg | Route | Schedule | | | | PR | CR | TFS | vs G1 | vs G2 | vs G3 | vs G4 |
| 1 | NT | --- | --- | --- | 14 | --- | --- | 0 | 0 | 0 | --- | --- | --- | --- |
| 2 | Irinotecan | 50 | IV | q7dx3 | 30 | 16 | 113 | 0 | 0 | 0 | *** | --- | --- | --- |
| 3 | Irinotecan | 100 | IV | q7dx3 | 29 | 15 | 103 | 0 | 0 | 0 | *** | --- | --- | --- |
| 4 | Irinotecan | 150 | IV | q7dx3 | 26 | 12 | 82 | 1 | 0 | 0 | *** | --- | --- | --- |
| 5 | Cmpnd I | 50 | IV | q7dx3 | 49 | 34 | 242 | 5 | 5 | 3 | *** | *** | --- | --- |
| 6 | Cmpnd I | 100 | IV | q7dx3 | 46 | 32 | 225 | 2 | 8 | 1 | *** | *** | *** | --- |
| 7 | Cmpnd I | 150 | IV | q7dx3 | 48 | 33 | 235 | 1 | 9 | 3 | *** | *** | --- | *** |
| 8 | Cisplatin | 10 | IP | q7dx3 | 15 | 1 | 7 | 0 | 0 | 0 | NS | --- | --- | --- |
| 9 | Carboplatin | 100 | IP | q7dx3 | 17 | 3 | 21 | 0 | 0 | 0 | NS | --- | --- | --- |

FIG. 3

COMPOSITIONS AND METHODS FOR ACHIEVING SUSTAINED THERAPEUTIC DRUG CONCENTRATIONS IN A SUBJECT

CROSS REFERENCE TO RELATED APPLICATIONS

This application is a continuation of U.S. patent application Ser. No. 14/555,440, filed Nov. 26, 2014, now U.S. Pat. No. 9,801,873, which is a continuation of U.S. patent application Ser. No. 13/120,551, filed Jun. 6, 2011, now U.S. Pat. No. 8,906,353, which is a 35 U.S.C. § 371 application of International Application No. PCT/US2009/005284, filed 23 Sep. 2009, designating the United States, which claims the benefit of priority under 35 U.S.C. § 119(e), which claims priority to the following U.S. Provisional Patent Applications: U.S. Provisional Patent Application No. 61/173,433 filed 28 Apr. 2009; U.S. Provisional Patent Application No. 61/106,931filed 20 Oct. 2008; and U.S. Provisional Patent Application No. 61/099,516 filed 23 Sep. 2008, all of which are incorporated herein by reference in their entireties.

FIELD

This invention relates to compounds and methods for achieving a sustained therapeutic effect of small molecule anti-cancer agents when administered in vivo.

BACKGROUND

Over the years, numerous methods have been proposed for improving the delivery of biologically active agents, and in particular, small molecule anticancer compounds. Challenges associated with the formulation and delivery of cancer chemotherapeutics can include poor aqueous solubility, toxicity, low bioavailability, instability, and rapid in-vivo degradation, to name just a few. Although many approaches have been devised for improving the delivery of anticancer compounds, no single approach is without its significant drawbacks. For instance, commonly employed drug delivery approaches aimed at solving or at least ameliorating one or more of these problems include drug encapsulation, such as in a liposome, polymer matrix, or unimolecular micelle, covalent attachment to a water-soluble polymer such as polyethylene glycol, use of gene targeting agents, nanoparticles, and the like.

The clinical effectiveness of many small molecule therapeutics, and oncolytics in particular, is limited by several factors. For instance, irinotecan and other camptothecin derivatives undergo an undesirable hydrolysis of the E-ring lactone under alkaline conditions. Additionally, administration of irinotecan causes a number of troubling side effects, including leucopenia, neutropenia, and diarrhea. Due to its severe diarrheal side-effect, the dose of irinotecan that can be administered in its conventional, unmodified form is extremely limited, thus hampering the efficacy of this drug and others of this type. Such harsh side effects, when severe, can be sufficient to arrest further development of such drugs as promising therapeutics. Additional challenges facing small molecule oncolytics include high clearance rates and minimal tumor permeation and residence time. Indeed, many chemotherapies are often accompanied by ultimate failure. Thus, the design and development of biocompatible delivery systems for anticancer compounds, as well as related therapeutic methods continues to present a significant challenge. Such challenge is met by the compounds and methods provided herein.

SUMMARY

In one aspect, the present disclosure is based at least in part upon the Applicant's surprising discovery of small molecule anticancer prodrugs that are effective to release an active moiety in vivo, wherein the effective half life in humans of the active moiety is greater than 50 hours.

In one embodiment of the foregoing, the prodrug effectively achieves metronomic dosing in vivo upon a single administration. Illustrative examples of a single administration include parenteral administration (including intraperitoneal, intravenous, subcutaneous, or intramuscular injection), oral, rectal, topical, nasal, and ophthalmic administration as well as an infusion with a pump over, for example, a period of 30 to 120 minutes.

Thus, provided herein is a method of achieving a metronomic dosing profile in vivo upon a single administration of a topoisomerase inhibitor prodrug. The method comprises administering a prodrug of a topoisomerase inhibitor to a mammalian subject (such as a human), wherein the topoisomerase inhibitor is releasably attached to a polyethylene glycol moiety, to thereby achieve in a single dose of the prodrug, plasma levels of the topoisomerase inhibitor or a metabolite thereof that remain above the level of detection for at least seven days post administration.

In one embodiment, plasma levels of the topoisomerase inhibitor or a metabolite thereof that remain above a level of detection that is at about 0.5 ng/mL.

In yet another embodiment, plasma levels of the topoisomerase inhibitor or a metabolite thereof that remain above a level of detection that is at about 1.0 ng/m L.

In yet another embodiment, plasma levels of the topoisomerase inhibitor or a metabolite thereof that remain above a level of detection that is at about 2.0 ng/m L.

In a related embodiment, the method or use of the prodrug is effective to achieve in a single dose of the prodrug, plasma levels of the topoisomerase inhibitor or a metabolite thereof that remain at least about two times above the level of detection for at least seven days post administration, or even remain at least about three times above the level of detection for at least seven days post administration.

In certain embodiments, the method or use of the prodrug is effective to achieve in a single dose of the prodrug, plasma levels of the topoisomerase inhibitor or a metabolite thereof that remain above the level of detection for at least 21 days post administration.

In yet one or more further embodiments, the method is effective o thereby achieve in a single dose of the prodrug, plasma levels of the topoisomerase inhibitor or a metabolite thereof that remain above the level of detection for at least seven days post administration, such as achieved by daily metronomic dosing of the topoisomerase inhibitor at a daily dosage amount that is at least two times lower than the dosage amount of topoisomerase inhibitor administered in prodrug form in the administering step.

In one or more embodiments related to the foregoing, the mode of administering is selected from intraperitoneal, intravenous, subcutaneous, and intramuscular injection.

In one exemplary embodiment, the prodrug is of a topoisomerase inhibitor such as but not limited to irinotecan, topotecan, camptothecin, or lamellarin D.

In yet another exemplary embodiment, the prodrug is of a microtubule inhibitor such as but not limited to vincristine, vinblastine, vinflunine, and docetaxel.

In yet a further embodiment, the prodrug is an irinotecan prodrug.

In yet another embodiment, the prodrug is multi-armed.

In a more specific embodiment, the multi-armed prodrug possesses from 3-10 polyethylene glycol arms each having a topoisomerase inhibitor molecule releasably attached thereto.

In an even more particular embodiment of any one or more of the foregoing, the prodrug has the structure:

Structure (I)

In yet an additional embodiment directed to administering a prodrug of irinotecan as described herein, the method is effective to achieve via the administering step, plasma levels of irinotecan or a metabolite thereof that remain above about 0.2 ng/mL for at least seven days post administration.

In a further embodiment, the prodrug, when administered in vivo, provides a desired concentration-time profile to achieve a desired pharmacodynamic effect, wherein the desired pharmacodynamic effect is different from the known (or understood or accepted) pharmacodynamic effect of the active moiety.

In a related embodiment of the foregoing method, the prodrug is of irinotecan, where the desired pharmacodynamic effect is antiangiogenesis, and the known pharmacodynamic effect is topoisomerase inhibition. In yet another related embodiment, the prodrug is of docetaxel, where the desired pharmacodynamic effect is antiangiogenesis, and the known pharmacodynamic effect is microtubule inhibition.

In yet another embodiment, the effective half life in humans of the active moiety is selected from the group consisting of half lives greater than 7 days, 10 days, 14 days, 20 days, 21 days, 25 days, 28 days, 30 days, 35 days, 40 days, 45 days, 49 days, 50 days, 60 days, 70 days, 80 days, 90 days, and 100 days.

In yet another particular embodiment, the prodrug is of a small molecule selected from the group consisting of platins, oxymorphone analogues, steroids, quinolones, and nucleosides.

In yet a further and more particular embodiment, the prodrug is of the small molecule, irinotecan.

In a second aspect, provided herein is a method of achieving sustained exposure to SN-38 via administration of irinotecan to a mammalian subject. The method comprises administering via a non-continuous dosing regimen to a mammalian subject having one or more cancerous solid tumors, a therapeutically effective amount of a pharmaceutical composition comprising a prodrug corresponding to structure (I):

Structure (I)

wherein the non-continuous dosing regimen comprises administering the pharmaceutical composition no more frequently than once every seven days, to thereby maintain sustained therapeutic levels of SN-38 in plasma between dosings.

In one embodiment, the therapeutic levels of SN-38 remain at or above a plasma concentration of about 0.2 ng/mL.

In one or more additional embodiments, the therapeutic levels of SN-38 remain at or above a plasma concentration selected from the group consisting of about 0.3 ng/mL, about 0.4 ng/mL, and about 0.5 ng/mL.

In yet a further embodiment, the dosing regimen comprises administering the pharmaceutical composition once every 21 days and the therapeutic levels of SN-38 remain at or above a plasma concentration of about 0.4 ng/mL between dosings.

In a third aspect, provided herein is a method for achieving extended therapeutic efficacy of irinotecan upon administration. The method comprises administering to a mammalian subject having one or more cancerous solid tumors, a therapeutically effective amount of a pharmaceutical composition comprising a prodrug corresponding to structure (I):

Structure (I)

wherein the administering comprises administering the composition at a frequency of between once every 7 days to once every 30 days, to thereby achieve an elimination half-life in plasma of SN-38 that exceeds 750 hours.

In one embodiment directed at least to the third aspect, the elimination half-life in plasma of SN-38 exceeds 900 hours.

In yet a further embodiment, the elimination half-life in plasma of SN-38 exceeds 1000 hours.

In yet another embodiment, the elimination half-life in plasma of SN-38 exceeds 1100 hours.

The following embodiments are directed to the foregoing second and third aspects as set forth above.

In one embodiment, the overall nominal average molecular weight of the prodrug ranges from about 10,000 to about 60,000 daltons. For example, the overall nominal average molecular weight of the prodrug is selected from about 10,000 daltons, 20,000 daltons, 30,000 daltons, 40,000 daltons, 50,000 daltons and 60,000 daltons.

In yet another embodiment, dosing occurs at a frequency selected from once every 7 days, once every 14 days, once every 21 days and once every 28 days.

In additional embodiments, the solid tumor type is selected from ovarian, breast, cervical, maxillary sinus, bladder, colorectal, small cell lung, and non-small cell lung.

In yet an additional embodiment, the administering comprises administering to the subject a dosage amount of irinotecan ranging from about 70 mg/m$^2$ to about 300 mg/m$^2$.

In yet another embodiment, the administering is intravenous.

In yet a further embodiment, the administering is effective to prevent tumor growth as measured from the start of treatment.

In yet an additional embodiment, the administering is effective to result in tumor size regression.

In a related embodiment, the administering is effective to result in tumor size regression of at least 20%.

In yet another aspect, provided herein is a method for treating a human subject having a cancer that was refractory to treatment with one or more anticancer agents, by administering a therapeutically effective amount of a topoisomerase inhibitor prodrug as described herein.

In a related embodiment, the human subject is one whose cancer was previously resistant to treatment with 1, or 2, or 3, or 4, or 5 or more anticancer agents. That is to say, in prior treatments, progression of the cancer was observed, while upon administration of a therapeutically effective amount of an exemplary prodrug, e.g., in one embodiment, compound I, anti-tumor activity was observed, either by virtue of partial tumor regression, arrestment of tumor growth, or by evidence provided by one or more biomarkers.

Additional methods include treatment of (i) metastatic breast cancer that is resistant to anthracycline and/or taxane based therapies, (ii) platinum-resistant ovarian cancer, (iii) metastatic cervical cancer, and (iv) colorectal cancer in patients with K-Ras mutated gene status by administering a therapeutically effective amount of a prodrug of a topoisomerase inhibitor molecule as described herein.

In one embodiment, the prodrug is one in which a topoisomerase inhibitor is releasably attached to a polyethylene glycol moiety.

In yet another aspect, provided is a method for treating metastatic breast cancer in which a topoisomerase inhibitor prodrug as described herein is administered to a patient with locally advanced metastatic breast cancer at a therapeutically effective amount, where the patient has had no more than two prior (unsuccessful) treatments with anthracycline and/or taxane based chemotherapeutics.

In yet a further aspect, provided is a method for treating platinum resistant ovarian cancer. In the method, a topoisomerase inhibitor prodrug as described herein is administered to a patient with locally advanced or metastatic ovarian cancer at a therapeutically effective amount, where the patient has shown tumor progression during platinum-based therapy. In one particular embodiment, the patient has had a progression-free interval of less than six months.

An exemplary compound for use in any one or more of the methods described herein corresponds to structure I.

In yet another approach, a topoisomerase inhibitor prodrug as provided herein (e.g., such as that in Example 1) is administered to a subject with locally advanced colorectal cancer, where the colorectal tumor(s) has a K-Ras oncogene mutation (K-Ras mutant types) such that the tumor does not respond to EGFR-inhibitors, such as cetuximab. Subjects are those having failed one prior 5-FU containing therapy, and are also irinotecan naïve.

Also provided are uses of the subject prodrugs in any one or more of the above described methods.

Additional embodiments of the present prodrugs, related compositions and methods will be apparent from the following description, drawings and examples. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present disclosure.

These and other objects and features will become more fully apparent when read in conjunction with the following detailed description.

DETAILED DESCRIPTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

All publications, patents and patent applications cited herein, whether supra or infra, are hereby incorporated by reference in their entirety.

Definitions

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

The following terminology will be used in accordance with the definitions described below.

"PEG" or "poly(ethylene glycol)" as used herein, is meant to encompass any water-soluble poly(ethylene oxide). Typically, PEGs for use in the present invention will comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. The variable (n) is 3 to 3000, and the terminal groups and architecture of the overall PEG may vary. When PEG or a conjugate comprising a PEG segment further comprises a spacer or a linker as in structure I above (to be described in greater detail below), the atoms comprising the spacer (X) or linker (Q), when covalently attached to a PEG segment, do not result in formation of (i) an oxygen-oxygen bond (—O—O—, a peroxide linkage), or (ii) a nitrogen-oxygen bond (N—O, O—N). PEGs for use in the invention include PEGs having a variety of molecular weights, structures or geometries to be described in greater detail below.

"Water-soluble", in the context of a polymer of the invention or a "water-soluble polymer segment" is any segment or polymer that is soluble in water at room temperature. Typically, a water-soluble polymer or segment will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

"Molecular mass" in the context of a water-soluble polymer of the invention such as PEG, refers to the nominal average molecular mass of a polymer, typically determined by size exclusion chromatography, light scattering techniques, or intrinsic viscosity determination in water or organic solvents. Molecular weight in the context of a water-soluble polymer, such as PEG, can be expressed as either a number-average molecular weight or a weight-average molecular weight. Unless otherwise indicated, all references to molecular weight herein refer to the number-average molecular weight. Both molecular weight determinations, number-average and weight-average, can be measured using gel permeation chromatographic techniques. Other methods for measuring molecular weight values can also be used, such as the use of end-group analysis or the measurement of colligative properties (e.g., freezing-point depression, boiling-point elevation, or osmotic pressure) to determine number-average molecular weight or the use of light scattering techniques, ultracentrifugation or viscometry to determine weight-average molecular weight. The polymers of the invention are typically polydisperse (i.e., number-average molecular weight and weight-average molecular weight of the polymers are not equal), possessing low polydispersity values such as less than about 1.2, less than about 1.15, less than about 1.10, less than about 1.05, and less than about 1.03. As used herein, references will at times be made to a single water-soluble polymer having either a weight-average molecular weight or number-average molecular weight; such references will be understood to mean that the single-water soluble polymer was obtained from a composition of water-soluble polymers having the stated molecular weight.

"Multi-armed" in reference to the geometry or overall structure of a polymer refers to polymer having 3 or more polymer-containing "arms" connected to a "core" molecule or structure. Thus, a multi-armed polymer may possess 3 polymer arms, 4 polymer arms, 5 polymer arms, 6 polymer arms, 7 polymer arms, 8 polymer arms or more, depending upon its configuration and core structure. One particular type of highly branched polymer is a dendritic polymer or dendrimer, that, for the purposes of the invention, is considered to possess a structure distinct from that of a multi-armed polymer. That is to say, a multi-armed polymer as referred to herein explicitly excludes dendrimers.

A "dendrimer" is a globular, size monodisperse polymer in which all bonds emerge radially from a central focal point or core with a regular branching pattern and with repeat units that each contribute a branch point. Dendrimers are typically formed using a nano-scale, multistep fabrication process. Each step results in a new "generation" that has two or more times the complexity of the previous generation. Dendrimers exhibit certain dendritic state properties such as core encapsulation, making them unique from other types of polymers.

"Branch point" refers to a bifurcation point comprising one or more atoms at which a polymer splits or branches from a linear structure into one or more additional polymer arms. A multi-arm polymer may have one branch point or multiple branch points, so long as the branches are not regular repeats resulting in a dendrimer.

"Active agent" as used herein includes any agent, drug, compound, and the like which provides some pharmacologic, often beneficial, effect that can be demonstrated in-vivo or in vitro. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of an active agent present in a pharmaceutical preparation that is needed to provide a desired level of active agent and/or conjugate in the bloodstream or in a target tissue or site in the body. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

The terms "subject", "individual" or "patient" are used interchangeably herein and refer to a vertebrate, preferably a mammal. Mammals include, but are not limited to, murines, rodents, simians, humans, farm animals, sport animals and pets. Such subjects are typically suffering from or prone to a condition that can be prevented or treated by administration of a polymer of the invention, typically but not necessarily in the form of a polymer-active agent conjugate as described herein.

"Metronomic" dosing refers to administration of comparatively low loses of drug, typically a chemotherapeutic, on a frequent or continuous schedule, with no extended interruptions. Generally, a metronomic dose is a lower dose than that administered using conventional therapy, e.g., a dose that is about 10% to about 75% of the conventional dose, and is more typically around 10% to about 50% of a recommended dose administered using conventional therapy, when calculated to a daily dosage amount. Metronomic dosing typically involves daily oral and continuous infusion schedules.

The term "about", particularly in reference to a given quantity, is meant to encompass deviations of plus or minus five percent.

"Treatment" or "treating" of a particular condition includes: (1) preventing such a condition, i.e. causing the condition not to develop, or to occur with less intensity or to a lesser degree in a subject that may be exposed to or predisposed to the condition but does not yet experience or display the condition, (2) inhibiting the condition, i.e., arresting the development or reversing the condition.

"Optional" or "optionally" means that the subsequently described circumstance may or may not occur, so that the description includes instances where the circumstance occurs and instances where it does not.

A "small molecule" may be defined broadly as an organic, inorganic, or organometallic compound typically having a molecular weight of less than about 1000. Small molecules of the invention encompass oligopeptides and other biomolecules having a molecular weight of less than about 1000.

Small Molecule Anti-Cancer Prodrugs

As described generally above, the instant disclosure relates to small molecule anticancer prodrugs. A prodrug refers to a compound that is generally (but not necessarily) inactive and in a form altered from the active parent drug, where upon administration, the prodrug is metabolized in vivo into an active metabolite. Preferably, the prodrugs provided herein are water-soluble polymer conjugates of small molecule anticancer agents.

In one particular embodiment, the prodrug is a multi-armed polymer prodrug of a small molecule anticancer agent.

Typically, the total number average molecular weight of the overall multi-arm polymer portion of a polymer conjugate is about 1,000 daltons (Da) to about 100,000 Da, more preferably about 10,000 Da to about 60,000 Da, most preferably about 15,000 to about 60,000 Da. Multi-armed polymers having a number average molecular weight of about 5,000 Da, about 8,000 Da, about 10,000 Da, about 12,000 Da, about 15,000 Da, about 20,000 Da, about 25,000 Da, about 30,000 Da, about 35,000 Da, about 40,000 Da, about 45,000 Da, about 50,000 Da, and about 60,000 Da are particularly preferred. Multi-armed polymers having a molecular weight of 20,000 Da or greater, i.e., of about 20,000 Da, or 25,000 Da, or 30,000 Da, or 40,000 Da or 50,000 Da, or 60,000 Da, are particularly preferred for tumor-targeting applications. The actual molecular weight of the multi-armed polymer will depend, of course, on the number of polymer arms and the molecular weight of each polymer arm in the overall multi-armed polymer.

Since they are prodrugs, in the case of a conjugates such as a water soluble polymer conjugate, the linkage between the polymer portion and the small molecule anticancer agent is preferably hydrolytically degradable for in vivo release of the parent drug molecule over time. Representative hydrolytically degradable linkages include carboxylate ester, carbonate ester, phosphate ester, anhydride, acetal, ketal, acyloxyalkyl ether, imine, orthoester, and oligonucleotides. Esters such as carboxylate and carbonate esters are particularly preferred linkages. The particular linkage and linkage chemistry employed will depend upon the particular small molecule anticancer agent, the presence of additional functional groups within the active agent, and the like, and can be readily determined by one skilled in the art based upon the guidance presented herein.

With respect to the prodrugs provided herein, it is not necessary for the prodrug itself to exhibit biological activity, since the parent drug is released upon hydrolysis. However, in certain embodiments, the prodrug maintains at least a measurable degree of activity. That is to say, in some instances, a prodrug possesses anywhere from about 1% to about 100% or more of the specific activity of the unmodified parent compound. In a preferred embodiment, a prodrug as provided herein will possess one or more therapeutic advantages over the unmodified parent drug. That is to say, a prodrug as provided herein will possess from about 1% to about 100% bioactivity relative to the unmodified parent anticancer agent, prior to conjugation. Such activity may be determined using a suitable in-vivo or in-vitro model, depending upon the known activity of the particular parent compound. For anticancer drugs, in vivo anticancer activity is typically evaluated by comparison of growth rates of tumor implants in drug treated and control groups of athymic mice using well-established animal models or in human-based trials as described herein in the accompanying examples. For instance, in certain animal models, anticancer activity is indicated by slower tumor growth rates in the treated group relative to the control group (J. W. Singer, et al., Ann. N.Y. Acad. Sci., 922: 136-150, 2000). As can be seen In the accompanying examples, any one of a number of indicators may be employed to demonstrate anticancer activity: e.g., positive response to treatment as indicated by cessation of tumor growth or tumor size regression, particularly in cases where treatment with either well-established or investigational anticancer agents has proven unsuccessful (i.e., refractory cases of cancer), improved plasma half-lives, greatly extended/sustained exposure profiles, altered plasma profiles, and the like.

Additionally, the severity of the side effects associated with administration of the prodrugs of the invention is preferably comparable to, or even more preferably, is less than, the side effects associated with administration of the parent compound. In particular, preferred anticancer prodrugs, particularly those of an anticancer agent such as irinotecan, when administered to a patient, result in reduced leucopenia/neuteopenia and diarrhea when compared to the unmodified parent drug molecule. The severity of side effects of anticancer agents such as camptothecin and camptothecin-like compounds can be readily assessed (See, for example, Kado, et al., Cancer Chemotherapy and Pharmacology, Aug. 6, 2003). Administration of a prodrug as provided herein will typically result not only in improved efficacy, but also in reduced side effects (e.g., toxicity) such as those described above when compared to the parent drug.

Structural Features of Prodrugs

Preferred prodrugs are those comprising a multi-arm polymer, i.e., having three or more arms, and having the generalized structure:

as described in detail in Applicant's United States Patent Application No. 20050112088, the contents of which is hereby incorporated herein in its entirety. One particularly preferred conjugate is described in Examples 1 and 2.

In the above structure, R is an organic radical possessing from about 3 to about 150 carbon atoms, preferably from about 3 to about 50 carbon atoms, and even more preferably from about 3 to about 10 carbon atoms, optionally containing one or more heteroatoms (e.g., O, S, or N). In one embodiment, R possesses a number of carbon atoms selected from the group consisting of 3, 4, 5, 6, 7, 8, 9, and 10. R may be linear or cyclic, and typically, emanating therefrom are at least 3 independent polymer arms each having at least one active agent moiety covalently attached thereto. Looking at the above structure, "q" corresponds to the number of polymer arms emanating from "R".

Q is a linker, preferably one that is hydrolytically stable. Typically, Q contains at least one heteroatom such as O, or S, or NH, where the atom proximal to R in Q, when taken together with R, typically represents a residue of the core organic radical R. Illustrative examples are provided below. Generally, Q contains from 1 to about 10 atoms, or from 1 to about 5 atoms. More particularly, Q typically contains one of the following number of atoms: 1, 2, 3, 4, 5, 6, 7, 8, 9, or 10. In a particular embodiment, Q is O, S, or —NH—C(O)—.

$POLY_1$ represents a water-soluble and non-peptidic polymer as described in detail below.

X is a spacer that comprises a hydrolyzable linkage, where the hydrolyzable linkage is attached directly to the active agent, D. Typically, at least one atom of the hydrolyzable linkage is contained in the active agent, D, in its unmodified form, such that upon hydrolysis of the hydrolyzable linkage comprised within X, the active agent, D, is released. Generally speaking, the spacer, X, has an atom length of from about 4 atoms to about 50 atoms, or more preferably from about 5 atoms to about 25 atoms, or even more preferably from about 5 atoms to about 20 atoms. Representative spacers have a length of from about 5, 6, 7, 8, 9, 10, 11, 12, 13, 14, 15, 16, 17, 18, 19, or about 20 atoms.

In yet another particular embodiment, X possesses the structure: Y—Z, where Y is a spacer fragment covalently attached to Z, a hydrolytically degradable linkage. In certain embodiments, Z itself may not constitute a hydrolytically degradable linkage, however, when taken together with Y, or at least a portion of Y, forms a linkage that is hydrolytically degradable. Preferably, Y comprises $(CH_2)_a$—C(O)NH—$(CH_2)_{0,1}$—$(CH_2CH_2O)_{0-10}$.

Preferably, $R_x$ and $R_y$ in each occurrence are independently H or lower alkyl. In one embodiment, $R_x$ and $R_y$ are in each occurrence H. In yet another embodiment, a ranges from 0 to 5. In yet another embodiment, b ranges from 0 to 5. In yet another embodiment, c ranges from 0 to 10. In yet another embodiment, K is —C(O)—NH. Any of the embodiments described herein is meant to apply not only to generalized structure I, but also to extend to particular combinations of embodiments.

In yet another embodiment, $R_x$ and $R_y$ in each occurrence are H, a is 1, K is —C(O)—NH, and b is 0 or 1.

Representative examples of X include —$CH_2$—C(O)—NH—$CH_2$—C(O)O— (here, Y corresponds to —$CH_2$—C(O)—NH—$CH_2$— and Z corresponds to —C(O)—O—), and —$CH_2$—C(O)—NH—$(CH_2CH_2O)_2$—C(O)—O— (here, Y corresponds to —$CH_2$—C(O)—NH—$(CH_2CH_2O)_2$— and Z corresponds to —C(O)—O—).

Returning now to the above structure, D is an active agent moiety such as a small molecule, and q (the number of independent polymer arms) ranges from about 3 to about 50. Preferably, q ranges from about 3 to about 25. More preferably, q is from 3 to about 10, and possesses a value of 3, 4, 5, 6, 7, 8, 9, or 10.

In accordance with one embodiment of the invention, the conjugate comprises a polymer having from about 3 to about 25 small molecules covalently attached thereto. More particularly, the conjugate comprises a water soluble polymer having 3, 4, 5, 6, 7, 8, 9, 10, 11, 12, 13, 14, 15, 16, 17, 18, 19, 20, 21, 22, 23, 24, or 25 active agent molecules covalently attached thereto. In a further embodiment, the conjugate of the invention has from about 3 to about 8 active agent molecules covalently attached to the water-soluble polymer. Typically, although not necessarily, the number of polymer arms will correspond to the number of active agents covalently attached to the water soluble polymer.

In instances in which the prodrug comprises a polymer conjugate, the polymer portion is preferably a water-soluble and non-peptidic polymer. Any of a variety of polymers that are non-peptidic and water-soluble can be used to form a conjugate in accordance with the teachings herein. Examples of suitable polymers include, but are not limited to, poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(acrylic acid), poly(vinyl alcohol), polyphosphazene, polyoxazoline, poly(N-acryloylmorpholine), and copolymers, terpolymers, and mixtures of any one or more of the above.

Preferably, the polymer is a polyethylene glycol or PEG, and can be in any of a number of geometries or forms, including linear chains, branched, forked, or preferably, multi-armed. PEG typically comprises —$(CH_2CH_2O)_n$—, where n ranges from about 5 to about 400, preferably from about 10 to about 350, or from about 20 to about 300. In the multi-arm embodiments described here, each polymer arm typically has a molecular weight corresponding to one of the following: 200, 250, 300, 400, 500, 600, 700, 800, 900, 1000, 1500, 2000, 3000, 4000, 5000, 6000, 7000, 7500, 8000, 9000, 10000, 12,000, 15000, 17,500, 18,000, 19,000, 20,000 daltons or greater. Overall molecular weights for the multi-armed polymer configurations described herein (that is to say, the molecular weight of the multi-armed polymer as a whole) generally correspond to one of the following: 800, 1000, 1200, 1600, 2000, 2400, 2800, 3200, 3600, 4000, 6000, 8000, 12,000, 16,000, 20,000, 24,000, 28,000, 30,000, 32,000, 36,000, 40,000, 48,000, 60,000 or greater. Typically, the overall molecular weight for a multi-armed polymer of the invention ranges from about 800 to about 60,000 daltons, and preferably, from about 10,000 to about 60,000, or more preferably from about 20,000 to about 40,000 daltons.

Active Agent

Typically, the active agent moiety is a small molecule anticancer agent possessing a molecular weight of less than about 1000. In yet additional embodiments, the small molecule drug possesses a molecular weight of less than about 800, or even less than about 750. In yet another embodiment, the small molecule drug possesses a molecular weight of less than about 500 or, in some instances, even less than about 300. Preferred active agent moieties include anticancer agents. Particularly preferred are oncolytics such as those having at least one hydroxyl group.

One preferred class of active agents are the camptothecins. In one embodiment, a camptothecin for use in a prodrug or method provided herein corresponds to the structure:

wherein $R_1$-$R_5$ are each independently selected from the group consisting of hydrogen; halo; acyl; alkyl (e.g., $C_1$-$C_6$ alkyl); substituted alkyl; alkoxy (e.g., $C_1$-$C_6$ alkoxy); substituted alkoxy; alkenyl; alkynyl; cycloalkyl; hydroxyl; cyano; nitro; azido; amido; hydrazine; amino; substituted amino (e.g., monoalkylamino and dialkylamino); hydroxcarbonyl; alkoxycarbonyl; alkylcarbonyloxy; alkylcarbonylamino; carbamoyloxy; arylsulfonyloxy; alkylsulfonyloxy; —C($R_7$)=N—(O)$_i$—$R_8$ wherein $R_7$ is H, alkyl, alkenyl, cycloalkyl, or aryl, i is 0 or 1, and $R_8$ is H, alkyl, alkenyl, cycloalkyl, or heterocycle; and $R_9$C(O)O— wherein $R_9$ is halogen, amino, substituted amino, heterocycle, substituted heterocycle, or $R_{10}$—O—(CH$_2$)$_m$— where m is an integer of 1-10 and $R_{10}$ is alkyl, phenyl, substituted phenyl, cycloalkyl, substituted cycloalkyl, heterocycle, or substituted heterocycle; or $R_2$ together with $R_3$ or $R_3$ together with $R_4$ form substituted or unsubstituted methylenedioxy, ethylenedioxy, or ethyleneoxy; $R_6$ is H or OR', wherein R' is alkyl, alkenyl, cycloalkyl, haloalkyl, or hydroxyalkyl; and L is one exemplary site of attachment to a modifying moiety to provide the prodrug structure.

In one particular embodiment, D is irinotecan, where the H on the 20-position hydroxyl is absent in the final multi-armed prodrug conjugate.

More particularly, the anticancer agent may fall into one of a number of structural classes, including but not limited to small molecules, oligopeptides, protein mimetics, fragments, or analogues, steroids, nucleotides, oligonucleotides, and the like. Preferably, an active agent for use herein possesses a free hydroxyl, carboxyl, thio, amino group, or the like (i.e., "handle") suitable for modification to provide the desired prodrug. Preferably, the anticancer agent possesses at least one functional group suitable for forming a hydrolyzable linkage for forming a prodrug.

Alternatively, the drug is modified by introduction of a suitable "handle", preferably by conversion of one of its existing functional groups to a functional group suitable for formation of a hydrolyzable covalent linkage. Ideally, such a modification should not adversely impact the therapeutic effect or activity of the active agent to a significant degree. That is to say, any modification of an active agent to facilitate its conversion to a prodrug should result in no greater than about a 30% reduction of its bioactivity relative to the known parent active agent prior to modification.

Preferred anticancer agents include topoisomerase inhibitors such as but not limited to irinotecan, topotecan, camptothecin, and lamellarin D, and microtubule inhibitors such as but not limited to vincristine, vinblastine, vinflunine, and docetaxel. Additional anticancer agents include altretamine, bleomycin, capecitabine, carboplatin, carmustine, cladribine, cisplatin, cyclophosphamide, cytarabine, dacarbazine, dactinomycin, doxorubicin, imatinib, etoposide, fludarabine, fluorouracil, gemcitabine, hydroxyurea, idarubicin, ifosfamide, methotrexate, mitomycin, mitotane, mitoxantrone, and paclitaxel.

The above exemplary drugs are meant to encompass, where applicable, analogues, agonists, antagonists, inhibitors, isomers, polymorphs, and pharmaceutically acceptable salt forms thereof.

As described previously, one preferred class of active agents is the camptothecins. The term "camptothecin compound" as used herein includes the plant alkaloid 20(S)-camptothecin, as well as pharmaceutically active derivatives, analogues and metabolites thereof. Examples of camptothecin derivatives include, but are not limited to, 9-nitro-20(S)-camptothecin, 9-amino-20(S)-camptothecin, 9-methyl-camptothecin, 9-chloro-camptothecin, 9-flouro-camptothecin, 7-ethyl camptothecin, 10-methyl-camptothecin, 10-chloro-camptothecin, 10-bromo-camptothecin, 10-fluoro-camptothecin, 9-methoxy-camptothecin, 11-fluoro-camptothecin, 7-ethyl-10-hydroxy camptothecin (SN38), 10,11-methylenedioxy camptothecin, and 10,11-ethylenedioxy camptothecin, and 7-(4-methylpiperazinomethylene)-10,11-methylenedioxy camptothecin, 7-ethyl-10-(4-(1-piperdino)-1-piperdino)-carbonyloxy-camptothecin, 9-hydroxy-camptothecin, and 11-hydroxy-camptothecin. Particularly preferred camptothecin compounds include camptothecin, irinotecan, and topotecan.

Preferred camptothecin compounds are illustrated in the structure below wherein $R_1$-$R_5$ are each independently selected from the group consisting of hydrogen; halo; acyl; alkyl (e.g., $C_1$-$C_6$ alkyl); substituted alkyl; alkoxy (e.g., $C_1$-$C_6$ alkoxy); substituted alkoxy; alkenyl; alkynyl; cycloalkyl; hydroxyl; cyano; nitro; azido; amido; hydrazine; amino; substituted amino (e.g., monoalkylamino and dialkylamino); hydroxcarbonyl; alkoxycarbonyl; alkylcarbonyloxy; alkylcarbonylamino; carbamoyloxy; arylsulfonyloxy; alkylsulfonyloxy; —C($R_7$)=N—(O)$_i$—$R_8$ wherein $R_7$ is H, alkyl, alkenyl, cycloalkyl, or aryl, i is 0 or 1, and $R_8$ is H, alkyl, alkenyl, cycloalkyl, or heterocycle; and $R_9$C(O)O— wherein $R_9$ is halogen, amino, substituted amino, heterocycle, substituted heterocycle, or $R_{10}$—O—(CH$_2$)$_m$— where m is an integer of 1-10 and $R_{10}$ is alkyl, phenyl, substituted phenyl, cycloalkyl, substituted cycloalkyl, heterocycle, or substituted heterocycle; or $R_2$ together with $R_3$ or $R_3$ together with $R_4$ form substituted or unsubstituted methylenedioxy, ethylenedioxy, or ethyleneoxy; and $R_6$ is H or OR', wherein R' is alkyl, alkenyl, cycloalkyl, haloalkyl, or hydroxyalkyl.

Exemplary substituting groups include hydroxyl, amino, substituted amino, halo, alkoxy, alkyl, cyano, nitro, hydroxycarbonyl, alkoxycarbonyl, alkylcarbonyloxy, alkylcarbonylamino, aryl (e.g., phenyl), heterocycle, and glycosyl groups.

Other preferred active agents include platins, oxymorphone analogues, steroids, quinolones, isoquinolones, and fluoroquinolones, and nucleosides and nucleotides.

C. Pharmaceutical Compositions

The invention provides pharmaceutical formulations or compositions, both for veterinary and for human medical use, which comprise one or more prodrugs of the invention or a pharmaceutically acceptable salt thereof, typically with one or more pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient thereof. The compositions may also include polymeric excipients/additives or carriers, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in "Remington: The Science & Practice of Pharmacy", 19th ed., Williams & Williams, (1995), and in the "Physician's Desk Reference", 52nd ed., Medical Economics, Montvale, N.J. (1998), and in "Handbook of Pharmaceutical Excipients", Third Ed., Ed. A. H. Kibbe, Pharmaceutical Press, 2000.

The prodrugs of the invention may be formulated in compositions including those suitable for oral, rectal, topical, nasal, ophthalmic, or parenteral (including intraperitoneal, intravenous, subcutaneous, or intramuscular injection) administration. One preferred formulation is one suitable for intravenous administration. The compositions may conveniently be presented in unit dosage form and may be prepared by any of the methods well known in the art of pharmacy. All methods include the step of bringing the active agent or compound (i.e., the prodrug) into association with a carrier that constitutes one or more accessory ingredients. In general, the compositions are prepared by bringing the active compound into association with a liquid carrier to form a solution or a suspension, or alternatively, bring the active compound into association with formulation components suitable for forming a solid, optionally a particulate product, and then, if warranted, shaping the product into a desired delivery form. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter. Particularly preferred are sterile, lyophilized compositions that are reconstituted in an aqueous vehicle prior to injection.

A preferred formulation is a solid formulation comprising a multi-arm polymer prodrug where the active agent is irinotecan. The solid formulation comprises sorbitol and lactic acid, and is typically diluted with 5% dextrose injection or 0.9% sodium chloride injection prior to intravenous infusion.

The amount of prodrug in the formulation will vary depending upon the specific anticancer agent employed, its activity, the molecular weight of the prodrug, and other factors such as dosage form, target patient population, and other considerations, and will generally be readily determined by one skilled in the art. The amount of prodrug in the formulation will be that amount necessary to deliver a therapeutically effective amount of the anticancer compound to a patient in need thereof to achieve at least one of the therapeutic effects associated with the compound, e.g., treatment of cancer. In practice, this will vary widely depending upon the particular conjugate, its activity, the severity of the condition to be treated, the patient population, the stability of the formulation, and the like. Compositions will generally contain anywhere from about 1% by weight to about 99% by weight prodrug, typically from about 2% to about 95% by weight prodrug, and more typically from about 5% to 85% by weight prodrug, and will also depend upon the relative amounts of excipients/additives contained in the composition. More specifically, the composition will typically contain at least about one of the following percentages of prodrug: 2%, 5%, 10%, 20%, 30%, 40%, 50%, 60%, or more by weight.

Compositions of the present invention suitable for oral administration may be presented as discrete units such as capsules, cachets, tablets, lozenges, and the like, each containing a predetermined amount of the active agent as a powder or granules; or a suspension in an aqueous liquor or non-aqueous liquid such as a syrup, an elixir, an emulsion, a draught, and the like.

Formulations suitable for parenteral administration conveniently comprise a sterile aqueous preparation of the prodrug, which can be formulated to be isotonic with the blood of the recipient.

Methods

The prodrugs can be used to treat or prevent any condition responsive to treatment with the unmodified active agent in any animal, particularly in mammals such as humans. The prodrugs are particularly useful as chemotherapeutics, e.g., in the treatment of cancer.

The prodrugs of the invention are particularly useful as anticancer agents, i.e., have been shown to be effective in releasing an active moiety in vivo, where the effective half life in humans of the active moiety (which may be an active metabolite) is greater than 50 hours. Preferably, the effective half life is greater than 7 days, or 10 days, or 14 days, or 20 days, or 21 days, or 25 days, or 28 days, or 30 days, or 35 days, or 40 days, or 45 days, or 49 days, or 50 days, or 60 days, or 70 days, or 80 days, or 90 days, or 100 days.

The prodrugs of the invention, in particular, those where the small molecule drug is an anticancer agent such as a camptothecin compound as described herein or other oncolytic, are useful in treating solid type tumors such as breast cancer, ovarian cancer, colon cancer, gastric cancer, malignant melanoma, small cell lung cancer, non-small cell lung cancer, thyroid cancers, kidney cancer, cancer of the bile duct, brain cancer, cervical cancer, maxillary sinus cancer, bladder cancer, esophageal cancer, Hodgkin's disease, adrenocortical cancer, and the like. Additional cancers treatable with the prodrugs and methods provided herein include lymphomas, leukemias, rhabdomyosarcoma, neuroblastoma, and the like. As stated above, the prodrugs are particularly effective in targeting and accumulating in solid tumors. The prodrugs are also useful in the treatment of HIV and other viruses.

The prodrugs have also been shown to be particularly advantageous when used to treat patients having cancers shown to be refractory to treatment with one or more anticancer agents (see, e.g., Tables III and IV in Example 2). As shown in Example 2, the exemplary prodrugs provided herein exhibit anti-tumor activity in subjects whose cancer was previously shown to be resistant to treatment with 1, or 2, or 3, or 4, or 5 or more anticancer agents. That is to say, in prior treatments, progression of the cancer was observed, while upon administration of a therapeutically effective amount of the exemplary prodrug, compound I, anti-tumor activity was observed, either by virtue of partial tumor regression, arrestment of tumor growth, or by evidence provided by one or more biomarkers.

Methods of treatment comprise administering to a mammal in need thereof, e.g., a human, a therapeutically effective amount of a composition or formulation containing a prodrug as described herein.

Additional methods include treatment of (i) metastatic breast cancer that is resistant to anthracycline and/or taxane based therapies, (ii) platinum-resistant ovarian cancer, (iii) metastatic cervical cancer, and (iv) colorectal cancer in patients with K-Ras mutated gene status.

In treating metastatic breast cancer, a prodrug as provided herein is administered to a patient with locally advanced metastatic breast cancer at a therapeutically effective amount, where the patient has had no more than two prior (unsuccessful) treatments with anthracycline and/or taxane based chemotherapeutics.

For treating platinum resistant ovarian cancer, a prodrug as provided herein is administered to a patient with locally advanced or metastatic ovarian cancer at a therapeutically effective amount, where the patient has shown tumor progression during platinum-based therapy. In one particular embodiment, the patient has had a progression-free interval of less than six months. See, e.g., Example 3, describing the superior anti-tumor activity of the exemplary compound, 4-arm PEG-GLY-Irino-20K, in an animal model of metastatic platinum resistant ovarian cancer as well as in a clinical phase 1 study. Efficacy of the exemplary prodrug was clearly superior to the parent compound in both the animal model and the preliminary phase 1 results. Moreover, the efficacious nature of 4-arm PEG-GLY-Irino-20K in treating patients having undergone prior anti-cancer therapy indicates the surprising advantages of the prodrugs described herein over conventional anti-tumor agents such as cis-platin.

In yet another approach, a prodrug as provided herein (e.g., such as that in Example 1) is administered to a subject with locally advanced colorectal cancer, where the colorectal tumor(s) has a K-Ras oncogene mutation (K-Ras mutant types) such that the tumor does not respond to EGFR-inhibitors, such as cetuximab. Subjects are those having failed one prior 5-FU containing therapy, and are also irinotecan naïve.

In yet another aspect, the prodrug effectively achieves a metronomic dosing profile in vivo upon a single administration. See for example, FIG. 1., which illustrates the patients' exposure to the active metabolite of irinotecan, SN-38, upon administration of the exemplary prodrug, Compound I. As can be seen, while approved irinotecan dosing regimens of once weekly or once every 21 days result in low or non-existent (i.e., non-detectable) plasma concentrations of SN-38 for prolonged periods of time prior to administration of a subsequent dose, administration of the instant prodrugs is effective to achieve a sustained exposure to SN-38 that is similar to the exposure profile expected for a continuous IV infusion of irinotecan, yet is achieved by dosing only once every 3 weeks.

Exemplary pharmacokinetics and pharmacodynamics of metronomic dosing of irinotecan in metastatic colorectal cancer patients is described, e.g., in Allegrini, G., et al., *British Journal of Cancer* (2008), 98, 1312-1319. Exemplary metronomic doses of irinotecan explored were 1.4 mg/m$^2$ per day, 2.8 mg/m$^2$ per day, and 4.6 mg/m$^2$ per day, administered by continuous iv infusion. The resulting plasma levels observed for irinotecan, SN-38, and SN-38 glucuronide at the various dose levels remained above the level of detection. For example, SN-38 plasma levels remained at around 1 ng/ml at the lowest dose for up to 63 days, while at higher doses, plasma levels of SN-38 ranged between about 2-4 ng/mL over a dosing period of 63 days. Similarly, for irinotecan, plasma levels over the dosing schedule ranged from about 100 ng/ml to about 250 ng/ml for the lowest dose amount, and from about 10 ng/ml to about 500 ng/ml over the 63 day time course observed for the higher doses. In each case, the plasma levels observed for the metronomic dosing schedules were fairly continuous and steady over time, and did not drop below therapeutic levels over the time course, in contrast to conventional dosing in which immediately after dosing, plasma levels of the anticancer drug or active metabolite thereof begin to steadily decline over time, eventually dropping below levels of detection.

In some instances, the prodrug, when administered in vivo, provides a desired concentration-time profile to achieve a desired pharmacodynamic effect, wherein the desired pharmacodynamic effect is different from the known (or understood or accepted) pharmacodynamic effect of the active moiety. For example, the prodrug is a prodrug of irinotecan, where the desired pharmacodynamic effect is antiangiogenesis, and the known pharmacodynamic effect is topoisomerase inhibition. Alternatively, the prodrug is a prodrug form of docetaxel, where the desired pharmacodynamic effect is antiangiogenesis, and the known pharmacodynamic effect is microtubule inhibition.

A therapeutically effective dosage amount of any specific prodrug will vary from conjugate to conjugate, patient to patient, and will depend upon factors such as the condition of the patient, the activity of the particular active agent employed, the type of cancer, and the route of delivery.

For camptothecin-type active agents, dosages from about 0.5 to about 100 mg camptothecin/kg body weight, preferably from about 10.0 to about 60 mg/kg, are preferred. When administered conjointly with other pharmaceutically active agents, even less of the prodrug may be therapeutically effective. For administration of a prodrug of irinotecan, the dosage amount of irinotecan will typically range from about 50 mg/m$^2$ to about 350 mg/m$^2$.

Methods of treatment are meant to encompass both monotherapy with a single prodrug, as well as administration of a therapeutically effective amount of a prodrug as described herein in conjunction with a second anticancer agent. for example, a camptothecin type prodrugs is administered in combination with 5-fluorouracil and folinic acid, as described in U.S. Pat. No. 6,403,569.

The prodrugs of the invention may be administered once or several times a day, preferably once a day or less, or once a week or less. Illustrative dosing regimens include dosing of a therapeutic amount of prodrug once every 7 days, or once every 14 days, or once every 21 days, or once every 28 days. The duration of the treatment may continue for a period of one month to several years. For example, the course of treatment may extend over one month, two months, three months, four months, five months, or six months, or even longer. Each dose can be administered either by a single dose in the form of an individual dosage unit or several smaller dosage units or by multiple administration of subdivided dosages at certain intervals.

EXAMPLES

It is to be understood that while the invention has been described in conjunction with certain preferred specific embodiments thereof, the foregoing description as well as the examples that follow are intended to illustrate and not limit the scope of the invention. Other aspects, advantages and modifications within the scope of the invention will be apparent to those skilled in the art to which the invention pertains.

Example 1

Synthesis of Pentaerythritolyl-4-Arm-(PEG-1-M Ethylene-2 Oxo-Vinylamino Acetate Linked-Irinotecan)-20K ("4-Arm PEG-GLY-Irino-20K, or Compound I)

The synthesis of 4-arm PEG-GLY-Irino-20K (Compound I) has been previously described. See, e.g., Applicant's United States Patent Publication No. 2005-0112088, Example 1.

Example 2

Phase I Clinical Study in Patients Having Advanced Stages of Cancer

In the Phase 1 dose-escalation trial, the safety, pharmacokinetics and anti-tumor activity of Compound I monotherapy were evaluated in 44 patients with advanced solid tumors who had failed prior treatments or had no standard treatment available to them. Patients received 90-minute infusions of Compound I as follows: weekly for three weeks with the fourth week off (n=32); q 14 days or every two weeks (n=6); and q 21 days or every three weeks (n=6). Tumor responses were evaluated according to RECIST (Response Evaluation Criteria in Solid Tumors) criteria.

Doses ranged from 58 mg/m$^2$ to 230 mg/m$^2$ in the weekly dose schedule (weekly x3 Q4 weeks). In the every two week dose schedule (Q14 days) and every three week dose schedule (Q21 days), doses ranged from 145 mg/m$^2$ to 170 mg/m$^2$. Tumor regression, anti-tumor activity or prolonged disease stabilization was observed in a broad spectrum of cancer types, including breast, ovarian, cervical, bladder, non-small cell lung cancer, small cell lung cancer, adrenocortical, esophageal, maxillary sinus and Hodgkins lymphoma. Side effects of clinical significance observed in the first and second dose schedules were diarrhea and neutropenia, with diarrhea being the dose-limiting toxicity associated with Compound I. There was no significant diarrhea and neutropenia observed in the every three week (Q21 days) dose schedule.

TABLE 1

RESULTS OF COMPOUND I WEEKLY x3 Q4 WEEKS DRUG-RELATED TOXICITIES AS OBSERVED IN ANY COURSE

| Dose Level mg/m$^2$ | Enrolled | Median # Courses (range) | Diarrhea G3 | Diarrhea G4 | Neutropenia G3 | Neutropenia G4 |
|---|---|---|---|---|---|---|
| 58 | 3 | 2 (2-6) | 0 | 0 | 0 | 0 |
| 115 | 6 | 5+ (1-6) | 1 | 0 | 1 | 0 |
| 145 | 6 | 1 (0.33-4) | 2 | 0 | 3 | 0 |
| 173 | 14 | 2.5 (0.67-6) | 7 | 0 | 3 | 0 |
| 230 | 3 | 0.87 (0.33-1.87) | 3 | 0 | 1 | 0 |
| Total | 32 | | 13 | 0 | 8 | 0 |

Dose escalation continued per protocol until the MTD (maximum tolerated dose) of 230 mg/m$^2$ was reached. All 3 patients at this dose had dose limiting G3 diarrhea.
The lower dose cohort of 173 mg/m$^2$ was therefore expanded, delayed observation of G3 diarrhea (7/14 patients) necessitated expansion of the next lower cohort.
In the next lower dose cohort at 145 mg/m$^2$, 2/6 patients had coexistent G3 diarrhea and G3 neutropenia in course 1. Therefore, the next lower dose cohort was further evaluated.
In the next lower dose cohort of 115 mg/m$^2$, one patient's G3 diarrhea coincident to anti-diarrheal medication noncompliance was not considered dose limiting. Except for this one patient, the 115 mg/m$^2$ dose was well tolerated and subsequently declared as the RP2D for the weekly x3 q4 weeks schedule.

On the weekly x3q4 weeks, the MTD/RP2D was 115 mg/m$^2$ and toxicity was manageable. Visual disturbances (floaters) noted in 13 of 32 patients were transient and self-limiting.

TABLE 2

RESULTS OF COMPOUND I WEEKLY Q14 DAYS
DRUG-RELATED TOXICITIES AS OBSERVED IN ANY COURSE

| Dose Level mg/m$^3$ | En-rolled | Median # Courses (range) | Diar-rhea G3 | Diar-rhea G4 | Neutro-penia G3 | Neutro-penia G4 |
|---|---|---|---|---|---|---|
| 145 | 3 | 4 (3-7) | 3 | 0 | 0 | 1 |
| 170 | 3 | 4 (3-7) | 1 | 0 | 1 | 0 |
| 195 | 3 | 3 (2-4) | 0 | 0 | 0 | 0 |
| 220 | 1 | 3 | 0 | 0 | 0 | 0 |

2 patients had G2 alopecia.
1 patient had transient, self-limited visual disturbances (floaters) associated with dosing.

TABLE 3

RESULTS OF COMPOUND I WEEKLY Q21 DAYS-ONGOING
DRUG-RELATED TOXICITIES AS OBSERVED IN ANY CYCLE

| Dose Level mg/m$^3$ | En-rolled | Median # Courses (range) | Diar-rhea G3 | Diar-rhea G4 | Neutro-penia G3 | Neutro-penia G4 |
|---|---|---|---|---|---|---|
| 145 | 3 | 2 (1-4) | 0 | 0 | 0 | 0 |
| 170 | 3 | 3.7 (2-6) | 0 | 0 | 0 | 0 |
| 195 | 3 | ongoing | 0 | 0 | 0 | 0 |
| 220 | 3 | ongoing | 0 | 0 | 0 | 1 |
| 245 | 3 | ongoing | 1 | 0 | 0 | 0 |

1 patient had transient, self-limited visual disturbances (floaters) associated with dosing.

Sustained SN-38 Exposure and Half-life: Serial plasma concentrations of Compound I, irinotecan, active metabolite SN38 and SN38-glucuronide were quantified by LC-MS/MS at multiple time points. SN38 AUCs after Compound I administration were estimated for each patient with concentration-time profiles as predicted with a 2-compartment exponential-error population PK model implemented using Monolix v2.3. SN38 AUCs after patient specific dose/schedule/# of doses of irinotecan administered were predicted using a population PK model for irinotecan administration (Xie, R., et al., JCO. 2002:20(15), 3293-33-1).

Compound I exhibited extended pharmacokinetics in the Phase 1 trial. Specifically, administration of Compound I produced an increase in cumulative SN38 exposure that was up to several-fold (4.4-fold) higher than the exposure previously reported with irinotecan. SN38, a topoisomerase I inhibitor, is the active metabolite of irinotecan. The long 50-day half life of SN-38 following administration of Compound I results in plasma SN38 concentrations that are significantly more sustained between doses than are possible with irinotecan.

TABLE 4

SN-38 CL$_{TOT}$ BY DRUG AND DOSING REGIMEN

| Drug | Dose, mg/m$^2$ | Schedule | Cumulative Dose | AUC (0-4000) | CL = Dose/AUC |
|---|---|---|---|---|---|
| Irino | 350 | q 3 Wks | 2800 | 4508 | 0.621 |
| Irino | 125 | q Wk x 4 | 2000 | 3220 | 0.621 |
| Compound I | 50 | q Wk x 3 | 750 | 5227 | 0.143 |
| Compound I | 200 | q 3 Wks | 1600 | 10842 | 0.148 |

Plasma SN38 Cmax and AUC values increased in a linear fashion. Inter-patient variability in SN38 CL and V1 parameters ranged from ~40 to ~60%, similar to that reported for SN38 after irinotecan administration (Xie, R., et al., JCO. 2002:20(15); 3293-3301).

SN-38 CL$_{tot}$ is four times less in comparison to irinotecan following administration of Compound I. Even when dosed once every three weeks, the SN-38 CP-T profile appears similar to one achieved by continuous infusion.

Figure 1:
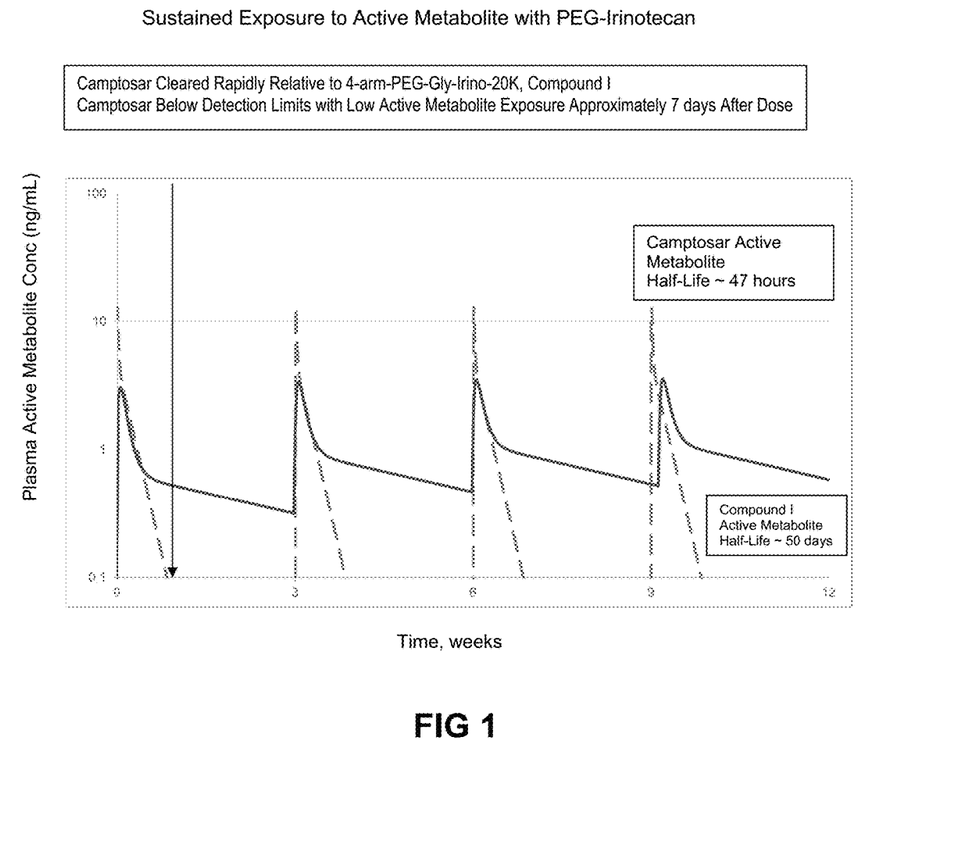
FIG. 1 is a graph illustrating sustained exposure to the active metabolite of irinotecan, SN-38, in human subjects administered a prodrug of irinotecan ("Compound I") on a 21 day dosing schedule (solid lines) in comparison to irinotecan (Camptosar®) as described in detail in Example 2. Specifically, the plot illustrates simulated SN-38 concentrations (ng/mL) over time (weeks) based upon the pharmacokinetic study described in Example 2.

See FIG. 1 which demonstrates sustained exposure to the active metabolite, SN-38, upon administration of Compound I, versus administration of irinotecan (Camptosar®). Camptosar® is cleared rapidly relative to Compound I—with plasma concentrations dropping below the level of detection by approximately 7 days (1 week) post-dosing. In contrast, administration of Compound I achieves prolonged exposure to therapeutically effective levels of SN-38 throughout each course of dosing, with plasma concentrations of SN-38 never observed to fall below the level of detection—even when measured at 21 days (3 weeks) post-dose. Sustained plasma SN38 concentrations are achieved upon administration of Compound I, even in the fourth (non-dosed) weeks of a weekly x3q4 weeks schedule. Roughly, it appears that upon dosing with Compound I, plasma concentrations of SN-38 remained above about 0.5 ng/mL, even at 21 days post-dosing! Cumulative SN38 exposures were approximately 2-fold greater than those predicted for irinotecan dosed at equivalent doses and schedules (mean 1.6, SD 0.8, min 0.6, max 4.4). Upon administration of Compound I, the effective half life of SN-38 was calculated to be approximately 50 days, while in contrast, the half-life of SN-38 achieved via administration of Camptosar® has been reported to be 47 hours.

FIG. 1 strikingly illustrates that while the active metabolite of Camptosar® is cleared relatively rapidly after administration (essentially dropping to below detection limits within 7 days following dosing), the plasma concentrations of the active metabolite of Compound I remain at detectable and even therapeutic levels over the course of duration of treatment—to at least 21 days post-dosing. As can be seen, the active metabolite of Compound I was determined to have a half-life of approximately 50 days, while the half life of the active metabolite of Camptosar® was determined to be approximately 47 hours.

TABLE 5 half-lives

| Parameter | Analyte | Population Estimate in Responding Patients | In Responding Patients |
|---|---|---|---|
| T$_{1/2}$ $\lambda_z$ (days) | Compound I | 7.4 days | 6.8-8.3 days |
|  | Irinotecan | 24.8 days | 19.2-34.1 days |
|  | SN-38 | 49.1 days | 14.4-98.3 days |

The differences in half-life and sustained plasma concentrations were striking between the two compounds, and demonstrated the surprising and unexpected clear superiority of Compound I as an anticancer agent.

Anti-Tumor Activity

Although the study was designed to evaluate safety, a notable number of patients surprisingly responded favorably to treatment by exhibiting either a cessation of tumor growth or a reversal (regression) of tumor size, where treatment with prior anti-cancer agents had failed. See Table 6 below.

TABLE 6

SIGNIFICANT ANTI-TUMOR ACTIVITY INCLUDES PARTIAL RESPONSES AND ADDITIONAL HIGH BIOMARKER ACTIVITY IN PHASE 1 STUDY

| Tumor | Dose, mg/m² Dosing Schedule | Anti-tumor Activity | # Courses to Response | Progression Observed with Prior Agents |
|---|---|---|---|---|
| Ovarian | 145 q14 days | PR: RECIST ↓ 48% ↓ CA-125 1900 U/ml → 150 U/ml | 2 | Investigational agent, docetaxel, carboplatin, tamoxifen, paclitaxel, cisplatin |
| Breast (triple negative) | 170 q21 days | PR: RECIST ↓ 41% | 2 | Bevacizumab, Doxil ®, docetaxel, cisplatin, gemcitabine, doxorubicin, cyclophosphamide |
| Cervical | 173 x3 q4 weeks | PR: RECIST ↓ 53% | 2 | Cisplatin, gemcitabine, pegaspargase (on a clinical trial) |
| Maxillary sinus (neuroendocrine) | 170 q14 days | PR: RECIST ↓ 35% and RECIST ↓ 45% | 2 4 | None |
| Bladder (transitional cell with small cell features) | 145 q14 days | PR: RECIST ↓ 35% and RECIST ↓ 53% | 2 4 | Cisplatin, gemcitabine, paclitaxel |
| Small cell lung | 58 x3 q4 weeks | PR: RECIST ↓ 56% | 2 | Investigational agent, gemcitabine, topotecan, carboplatin, etoposide, cisplatin |
| Non small cell lung | 145 x3 q4 weeks | PR: RECIST ↓ 52% | 1 | Pemetrexed, docetaxel, carboplatin |

PR = partial regression

Significant anti-tumor activity was observed in all dose schedules of the study with partial responses observed in seven out of 44 total patients (16 percent) in the trial. Of the 44 patients in total from all dose schedules, 13 patients exhibited anti-tumor activity. Seven patients, or 16 percent, had partial responses (greater than 30 percent tumor regression per RECIST), and six patients, or 12 percent, had other evidence of anti-tumor activity (tumor regression by more than 15 percent but less than 30 percent per RECIST, or significant biomarker evidence). Repeat evidence of anti-tumor activity was observed in a number of tumor settings, including breast and ovarian.

TABLE 7

BIOMARKER ACTIVITY IN PHASE 1 STUDY

| Tumor | Dose, mg/m² Dosing Schedule | Anti-tumor Activity | # Courses to Response | Progression Observed with Prior Agents |
|---|---|---|---|---|
| Breast (triple negative) | 145 q 14 days | CT scan ↓ 20% | 2 | doxorubicin, cyclophosphamide, XRT, Investigational agent, capecitabine plus bevacizumab |
| Breast (triple negative) | 170 q 14 days | ↓ CA 27.29 837 U/ml → 383 U/ml | 2 | docetaxel, cisplatin, gemcitabine, doxorubicin, cyclophosphamide, XRT, oxaliplatin |
| Ovarian | 173 x3 q4 weeks | ↓ CA-125 2558 U/ml → 518 U/ml | 0.6 | cisplatin, gemcitabine, carboplatin, paclitaxel |
| Esophageal | 58 x3 q4 weeks | ↓ CEA 36 ng/ml → 14 ng/ml PET scan response | 2 | cisplatin, carboplatin, paclitaxel, 5-FU |
| Hodgkin's Disease | 115 x3 q4 weeks | CT scan ↓ 14% ↓ LDH | 2 | ifosfamide, carboplatin, etoposide, topotecan, paclitaxel, doxorubicin, dacarbazine, bleomycin, vinblastine, |

TABLE 7-continued

BIOMARKER ACTIVITY IN PHASE 1 STUDY

| Tumor | Dose, mg/m² Dosing Schedule | Anti-tumor Activity | # Courses to Response | Progression Observed with Prior Agents |
|---|---|---|---|---|
| | | | | procarbazine, prednisone |

Example 3

Nonclinical and Phase 1 Clinical Anti-Tumor Activity in Platinum-Resistant Ovarian Cancers This study was undertaken to investigate the nonclinical and clinical anti-tumor activity of 4-arm PEG-GLY-Irino-20K (Compound I) in metastatic platinum resistant ovarian cancer.

Non-Clinical Protocol: Mice bearing A2780 ovarian tumors that are minimally responsive to cisplatin received Compound I or irinotecan in 3 weekly doses of 50, 100, or 150 mg/kg. Anti-tumor efficacy was evaluated based on tumor growth delay (TGD) in mice and response rate in mice and humans.

Specifically, A2780 tumor cells were grown in vitro and implanted s.c. as a cell suspension in 9 to 10 weeks old female nude mice (nu/nu, Harlan) weighing 18-26 g. When the tumor volume reached an average of 146 mm³, mice (n=10/treatment) were randomized into the treatment groups and treated with 3 weekly intravenous injections of irinotecan or Compound I, or 3 weekly intra-peritoneal administrations of cisplatin or carboplatin.

Animals were weighed and monitored twice weekly, and tumor volumes were measured until an endpoint was met (2000 mm³ or 60 days). Anti-tumor efficacy was evaluated based on tumor growth delay and response rate or partial or complete regression (PR or CR). In a PR, the tumor volume was 50% or less of its Day 1 volume for three consecutive measurements, and equal to or greater than 14 mm³ for one or more of these three measurements. In a CR, the tumor volume was less than 14 mm³ for three consecutive measurements. An animal with a CR response at termination was additionally classified as tumor-free survivior (TFS). A Student's T-test was performed to calculate statistical significance ($p<0.05$).

Clinical Protocol: In the phase 1 study of Compound I, 5 patients with ovarian cancer were enrolled in weekly ×3 q4w, q14d and q21d regimens. Patients with measurable disease were assessed for tumor response using RECIST 1.0 every other cycle.

Specifically, in an open-label, dose-escalation, multi-center Phase 1 study, patients with advanced solid tumors whose tumors had failed prior treatments were enrolled. The study enrolled a total of 72 patients, five of whom had ovarian cancer. Patients received 90-minute infusions of NKTR-102 on either a weekly ×3 every 4 weeks (qw×3 q4w), every 14 days (q14d), or every 21 days (q21d) schedule. Patients were evaluated for safety, pharmacokinetics and evidence of anti-tumor activity (by RESIST 1.0 guidelines).

Results

Figure 3:
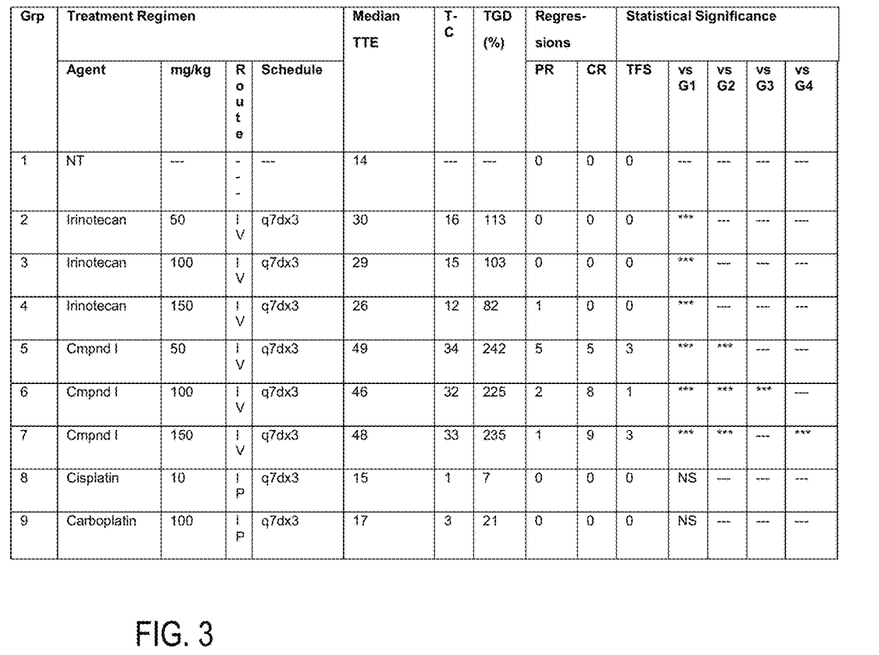
FIG. 3 is a table summarizing the agent administered, treatment regimen, route of administration, dosing schedule, tumor growth delay response, and other data related to the platinum resistant ovarian 2780 ovarian cancer model described above and in Example 3.

Mice: The response summary is provided in the table provided as FIG. 3. Control tumors grew rapidly and uniformly to the 2000 mm³ endpoint in a median of 14 days. Irinotecan administered at 50, 100, and 150 mg/kg resulted in TGD of 12, 15, and 16 days, respectively, with one partial response (PR) at the highest dose. Compound I when administered at irinotecan-equivalent doses resulted in TGDs of 33, 32, and 34 days, respectively, with 100% regression response rate (PRs+CRs) in each group. Increasing Compound I doses were associated with increased numbers of CR responses (5, 8, and 9 CRs, respectively). Compound I was superior to the equivalent irinotecan dose at all doses tested and the lowest dose of Compound I was superior to the highest irinotecan dose.

Figure 2:
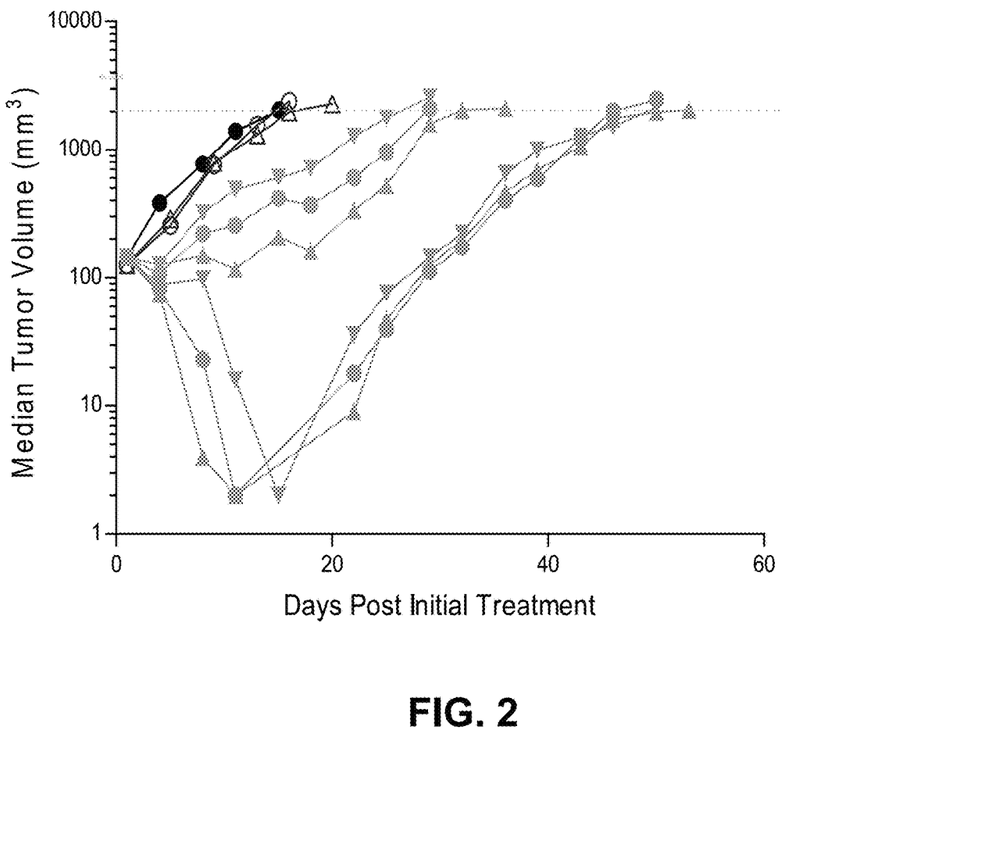
FIG. 2 is a graph illustrating median tumor volume (mm$^3$) versus days post initial treatment in a platinum resistant 2780 ovarian cancer model as described in detail in Example 3. Figure Legend: Closed circles, black (●): no treatment (top data plot)-endpoint reached prior to 20 days post-treatment; open circles (○): treatment with cisplatin, top plot next to the "no treatment" data, endpoint reached prior to 20 days post treatment; open triangles (Δ): treatment with carboplatin, plot nearly identical to cisplatin data, endpoint reached prior to 20 days post treatment; next three plots in center of graph—irinotecan data at center portion of graph, administered at varying doses: (closed triangles, grey (▼), 50 mg/kg irinotecan; closed circles, grey (●), 100 mg/kg irinotecan; and (closed upwards triangles, grey ▲), 150 mg/kg irinotecan—all reaching endpoint at approximately 30 days post initial treatment; final three plots of Compound I administered at varying doses, closed triangles, grey (▼), 50 mg/kg Compound I; closed circles, grey (●), 100 mg/kg Compound I; and closed upwards triangles, grey (▲), 150 mg/kg Compound I, all extending to greatest number of days to reach endpoint, e.g., approximately 50 days.

In summary, Compound I shows superior activity compared to irinotecan in the A2780 ovarian tumor model, inducing a 100% response rate at all doses and dose-related increases in CRs versus PRs. See FIG. 2. Control tumors grew to the 2000 mm3 endpoint in a median of 14 days, establishing a maximum possible tumor growth delay of 46 days (329%) for the 60 day study. Cisplatin and carboplatin were inactive. Further, Compound I was well tolerated, while irinotecan resulted in acute effects immediately after dosing (tremors, hypoactivity, ataxia, pilo-erection, increased stool production).

Humans: In the phase 1 clinical study, tumor response could be assessed in 2 of 5 patients. Of these two patients, one patient receiving 145 mg/m² q14 (sixth line) had an unconfirmed partial response (37% reduction in target lesions) but terminated from the study prior to confirmation, and one patient on the weekly regimen receiving 172.5 mg/m² had a mixed response that included a 21% reduction in target lesions.

The foregoing results indicate the superior nature of exemplary prodrug, 4-arm PEG-GLY-Irino-20K (Compound I), in comparison not only to irinotecan, but also to other forms of cancer therapy, namely cis-platin and carboplatin. The non-clinical data is striking in its results, and demonstrates the surprising efficacy and tolerability of the compounds and methods provided herein.

Many modifications and other embodiments will come to mind to one skilled in the art to which this disclosure pertains having the benefit of the teachings presented in the foregoing description. Therefore, it is to be understood that the disclosure is not to be limited to the specific embodiments disclosed and that modifications and other embodiments are intended to be included within the scope of the teachings herein. Although specific terms are employed herein, they are used in a generic and descriptive sense only and not for purposes of limitation.

It is claimed:

1. A method of treating a human subject having metastatic breast cancer, the method comprising administering via a non-continuous dosing regimen to the human subject, a therapeutically effective amount of a pharmaceutical composition comprising a prodrug of structure (I) or a pharmaceutically acceptable salt form thereof:

Structure (I)

wherein the non-continuous dosing regimen comprises administering the pharmaceutical composition no more frequently than once every seven days, to thereby maintain sustained therapeutic levels of greater than 0.4 ng/mL of SN-38 in plasma of the subject between dosings.

2. The method of claim 1, wherein the therapeutic levels of SN-38 remain at or above a concentration in plasma of about 0.5 ng/mL between closings.

3. The method of claim 1, wherein the dosing regimen comprises administering the pharmaceutical composition at a dosage amount of 145 mg/m² irinotecan once every 21 days.

4. The method of claim 1, wherein the overall nominal average molecular weight of the prodrug ranges from about 10,000 to about 60,000 daltons.

5. The method of claim 4, wherein the administering occurs at a frequency selected from once every 7 days, once every 14 days, once every 21 days and once every 28 days.

6. The method of claim 1, wherein the human subject has had no more than two prior treatments with anthracycline and/or taxane-based chemotherapeutics.

7. The method of claim 1, wherein the administering comprises administering to the human subject a dosage amount of irinotecan ranging from about 70 mg/m² to about 300 mg/m².

8. The method of claim 1, wherein the administering is effective to provide an anti-tumor effect as evidenced by partial tumor regression, arrestment of tumor growth, or by evidence provided by one or more biomarkers.

9. The method of claim 8, wherein the administering is effective to result in tumor size regression.

10. The method of claim 6, wherein the prior treatments with anthracycline and/or taxane-based chemotherapeutics were unsuccessful.

11. The method of claim 1, wherein the pharmaceutical composition is in a form suitable for intravenous administration.

12. The method of claim 11, wherein the administering is intravenous.

13. The method of claim 1, wherein the pharmaceutical composition comprises sorbitol and lactic acid.

* * * * *